United States Patent [19] [11] 4,386,614
Ryan [45] Jun. 7, 1983

[54] SYSTEM FOR COMPARING A REAL-TIME WAVEFORM WITH A STORED WAVEFORM

[75] Inventor: Gregory J. Ryan, King County, Wash.

[73] Assignee: Myo-Tronics Research Inc., Seattle, Wash.

[21] Appl. No.: 310,293

[22] Filed: Oct. 9, 1981

Related U.S. Application Data

[63] Continuation-in-part of Ser. No. 264,834, May 18, 1981, abandoned.

[51] Int. Cl.³ .............................................. A61B 5/00
[52] U.S. Cl. .................................. 128/777; 340/721; 340/722
[58] Field of Search ............... 128/655, 733, 745, 774, 128/777, 779, 781, 782; 179/15 A, 15 B, 15 C, 15 P; 340/715, 721, 722, 747; 346/33 M; 434/185

[56] References Cited

U.S. PATENT DOCUMENTS

| 2,416,353 | 2/1947 | Shipman et al. | 434/185 |
| 3,406,387 | 10/1968 | Werme | 340/744 |
| 3,522,597 | 8/1970 | Murphy | 340/722 |
| 3,881,059 | 4/1975 | Stewart | 179/1.5 P |
| 4,222,048 | 9/1980 | Johnson | 340/727 |
| 4,328,491 | 5/1982 | Demetrescu et al. | 340/747 |
| 4,342,086 | 7/1982 | Adib | 128/653 |

Primary Examiner—Richard J. Apley
Assistant Examiner—George Yanulis
Attorney, Agent, or Firm—Seed, Berry, Vernon & Baynham

[57] ABSTRACT

A system for storing time-varying kinesiograph waveforms and continuously displaying the stored waveforms on the screen of a cathode-ray tube (CRT). In a recording mode, the waveforms are periodically sampled, digitized, and then stored in a block of random access memory reserved for that waveform. In a display mode, the Y axis of the CRT is driven by a digital-to-analog converter which receives digitized samples from the memory block corresponding to the displayed waveform. The X axis of the CRT is driven by a second digital-to-analog converter, which, in an X-Y mode, also receives digitized samples from a selected block of memory. In a sweep mode, the X axis digital-to-analog converter receives the continuously incrementing memory addresses, which read out digitized samples from the memory block for the displayed waveform. The system may also display an expanded portion of a waveform in the sweep mode by incrementing the memory address from one of several predetermined values. In the X-Y mode, two pairs of kinesiograph waveforms may be displaced with respect to each other on the left and righthand sides of the CRT screen. A multiplexer for the X and Y axes allows a real-time kinesiograph waveform to be superimposed on the same stored waveform to facilitate mandibular movement comparisons. The system may also operate in a sensor positioning mode in which a line connecting the optimum position of the sensors and the current position of the sensors is generated on the screen of the CRT.

15 Claims, 11 Drawing Figures

SYSTEM FOR COMPARING A REAL-TIME WAVEFORM WITH A STORED WAVEFORM

CROSS-REFERENCE TO RELATED APPLICATION

This application is a continuation-in-part of U.S. patent application Ser. No. 264,834, filed May 18, 1981 now abandoned.

DESCRIPTION

1. Technical Field

This invention relates to dental diagnostic devices and, more particularly, to a system for displaying a set of real-time kinesiograph waveforms in superposition with a single set of the same kinesiograph waveforms occurring earlier in time.

2. Background Art

A kinesiograph, as described in U.S. Pat. No. 3,822,694, is a device for generating respective electrical signals indicative of the position of a patient's mandible in at least two orthogonal directions. Basically, a magnet is temporarily mounted beneath the lower lip of the patient and its position is sensed by magnetic sensors mounted on a frame worn by the patient. A kinesiograph presently used for diagnostic purposes generates respective waveforms indicative of the position of the magnet, and hence the mandible, in the anterior/posterior, lateral and vertical planes. It also generates a waveform indicative of the vertical velocity of the mandible.

The kinesiograph waveforms may be displayed in either a sweep mode or an X-Y mode. In the sweep mode, one or more kinesiograph waveforms are simultaneously displayed with respect to time. In the X-Y mode, one or more pairs of kinesiograph waveforms are displayed with respect to each other.

The kinesiograph is used for diagnostic purposes by comparing mandible movement over several cycles. Accordingly, it is necessary to continuously display the waveform from a previous mandibular movement while also displaying the waveform from subsequent mandibular movements as they occur. For this purpose, a conventional storage oscilloscope has been used in the past to record and display the kinesiograph waveforms on the screen of a CRT as each of the waveforms occurs. Alternatively, a conventional non-storage oscilloscope may be used in a non-storage mode by displaying the kinesiograph waveforms as they occur.

The principal disadvantage of using conventional storage scopes is the inability to display one stored waveform while the subsequent kinesiograph waveforms are viewed in a non-storage mode. Viewing all waveforms in a storage mode quickly causes the screen to be obscured by multiple waveforms overlapping each other. Accurate comparison of prior and subsequent kinesiograph waveforms under these conditions is extremely difficult. As a result, mandibular movement can be compared over only a relatively small number of cycles.

The frame on which the sensors are mounted should be positioned so that the magnetic sensors are symmetrically positioned with respect to the magnet. In the past, positioning has been accomplished by examining a single dot on the screen indicative of the magnet's position. This technique, while somewhat satisfactory if carefully performed, is nevertheless difficult, time-consuming, and inherently inaccurate.

DISCLOSURE OF THE INVENTION

The primary object of the invention is to display a single set of recorded kinesiograph waveforms in superposition with the same set of waveforms in real time as they occur.

It is another object of the invention to provide a circuit for ensuring that the same kinesiograph waveforms are superimposed on each other.

It is another object of the invention to provide a system for facilitating quick and accurate positioning of the magnetic sensors to achieve optimum results.

It is still another object of the invention to provide a device of the character described which exhibits a great deal of flexibility of use so that a wide variety of waveforms can be displayed in a variety of modes.

It is a further object of the invention to display stored kinesiograph waveforms in an expanded sweep mode so that any portion of the waveform can be closely examined.

These and other objects of the invention are provided by storage means for recording the real-time kinesiograph waveforms and repetitively generating respective output signals corresponding thereto. A display means then displays the kinesiograph signals on its screen in superposition with the corresponding output signals of the storage means. The storage means may include a random access memory divided into a plurality of memory blocks in which samples of respective kinesiograph waveforms are stored in locations identified by respective memory addresses. The display means may include a switch which selects one of the kinesiograph waveforms as an output and a multiplexer for alternately displaying the output of the switch and an analog signal indicative of the kinesiograph sample selected by the memory address. The switch determines most significant bits of the memory address, which identify a specific block of memory corresponding to the waveform selected by the switch. The storage means may further include a sample means and analog-to-digital converter for digitizing the kinesiograph waveforms and storing them in the random access memory. Digitized samples are read from the memory in one of two ways, depending upon the display mode selected. In a sweep mode, the digitized samples are read out in chronological order and displayed along the Y axis of the screen while the memory addresses are applied to a digital-to-analog converter having its output driving the X axis of the display. The kinesiograph signals are thus displayed with respect to time. In an expanded sweep mode, only a portion of the memory addresses are accessed so that the kinesiograph waveforms stored within those memory locations are examined in greater detail. In an X-Y mode, corresponding memory locations in each block of memory are accessed in sequence. The system can also display a line emanating from the center of the screen that indicates the magnitude and direction the frame should be moved to its optimum position.

Best Mode for Carrying Out the Invention

Figure 1:
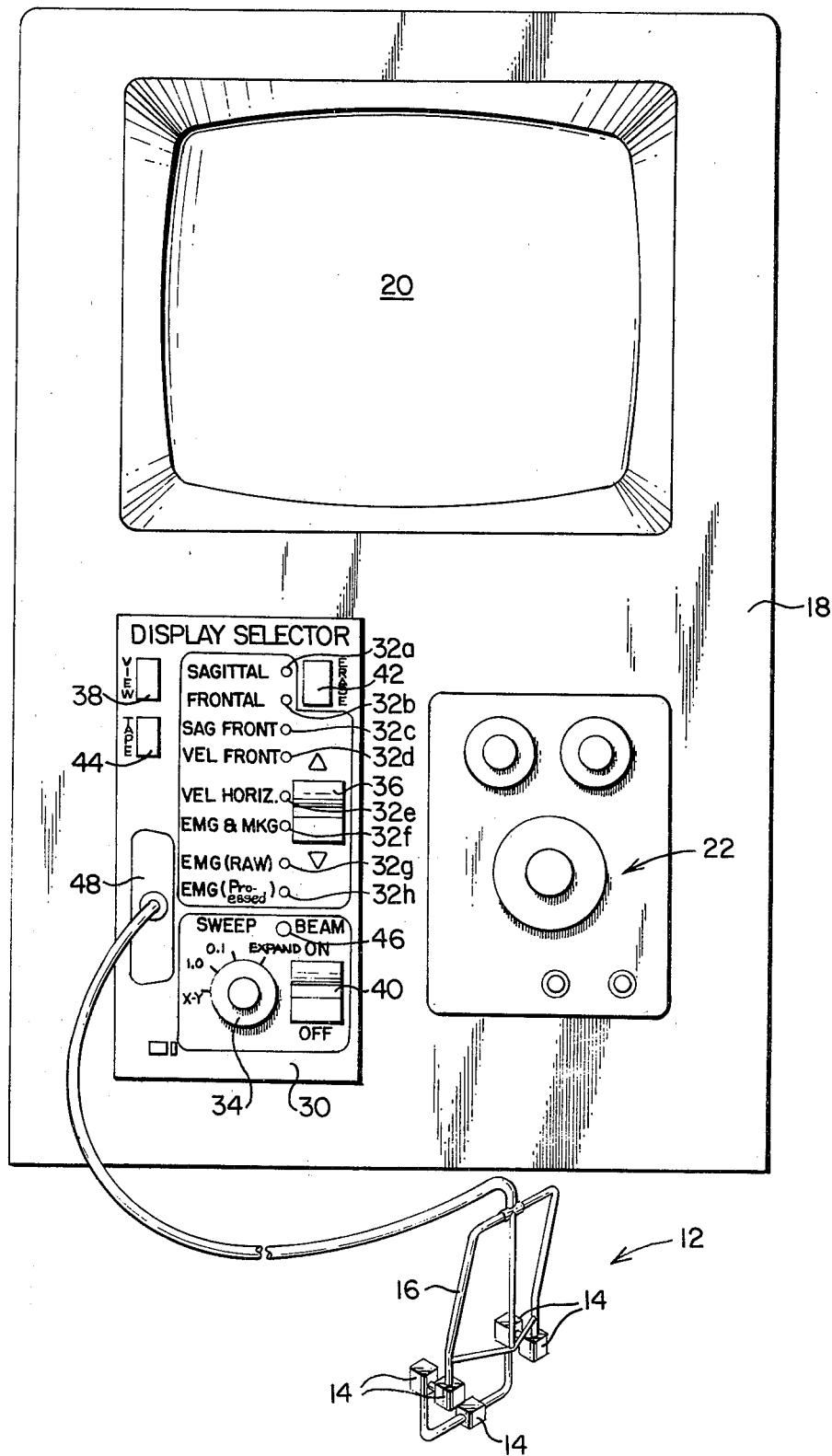
FIG. 1 is an isometric view of the storage and display device connected to a conventional kinesiograph.

One commercially available device with which the display system may be used is a kinesiograph, as illustrated in FIG. 1. Basically, the kinesiograph includes a headpiece 12 having an array of magnetic sensors 14 mounted on a frame 16. The frame 16 is place on the head of a patient and a small magnet is secured to the patient's mandible. The sensors 14 produce respective electrical indications of the position of the mandible in the lateral, anterior/posterior and vertical directions. The outputs of the sensors are applied to a kinesiograph display console 18 which has a cathode-ray tube screen 20 and appropriate manually adjustable controls indicated generally at 22. The sensors 14 are connected to the kinesiograph 18 through a conventional multiconductor cable 24. A more detailed description of the kinesiograph can be found in U.S. Pat. No. 3,822,694.

It will be seen that the sensors 14 on the frame 16 are essentially bilateral. In use, best results are obtained when the sensors 14 are symmetrically positioned with respect to the magnet secured to the patient's mandible. In the past, proper positioning was done by examining a single dot on the screen indicative of the position of the magnet. Often the frame was sufficiently misaligned so that the dot was displaced off of the screen. However, it is difficult and time-consuming to position the frame in this manner. As explained hereinafter, the system provides a unique indication to allow quick and accurate positioning of the frame 16.

The kinesiograph operates in one of two modes. In a sweep mode, either the lateral, vertical, anterior/posterior position or vertical velocity of the mandible is plotted as a function of time on the screen 20. In an X-Y mode, the vertical position of the mandible is displayed with respect to the position of the mandible in another plane on the lefthand side of the screen 20, and the position or velocity of the mandible in one plane is displayed with respect to the position of the mandible in another plane on the righthand side of the screen 20.

In using the kinesiograph for diagnostic purposes, it is generally desirable to view mandibular movement over a number of cycles and to accurately compare the position of the mandible in one plane with the position of the mandible in other planes. Diagnosis in this manner is therefore facilitated by utilizing a display having storage capability so that a display of mandibular movement for a previous cycle and in several planes is continuously displayed on the screen 20. In the past, the kinesiograph has utilized conventional storage oscilloscope technology to continuously display several cycles of mandibular movement. However, these existing storage scopes have not allowed the simultaneous display of one mandibular movement and several mandibular movements occurring in real time. Instead, the trace for each mandibular movement must be stored as it is viewed. After several traces have been stored, the previous traces obscure more recent traces, thus making accurate comparisons impossible. As explained in greater detail hereinafter, the inventive display system allows a single or several mandibular movements to be stored and cotinuously displayed while also displaying the real-time mandibular movements as they occur.

As further illustrated in FIG. 1, the system includes a control panel 30 having several lamps 32 providing an indication of which mandibular movements are being displayed. The manner in which these mandibular movements are displayed in controlled by selector knob 34, which, in its first position, selects an X-Y display; in its second position, selects a sweep of 1 sec/cm; in its third position, selects a sweep of 0.1 sec/cm; and in its fourth, position, expands the waveform viewed in the third position, thereby viewing only a portion of that waveform.

In the sagittal mode, indicated by lamp 32a, the vertical and anterior/posterior positions of the mandible are displayed. In the X-Y mode, the vertical position of the mandible is displayed along the Y axis and the anterior/posterior position of the mandible is displayed along the X axis. In the sweep mode, both the vertical and the anterior/posterior positions are displayed as a function of time.

In the frontal mode, indicated by lamp 32b, the vertical and lateral positions of the mandible are displayed. In the X-Y mode, the vertical position of the mandible is displayed along the Y axis and the lateral position of the mandible is displayed along the X axis. In the sweep mode, both the vertical and the lateral positions are displayed as a function of time.

In the sagittal/frontal mode, indicated by lamp 32c, mandible movement in both the sagittal and frontal planes are displayed. In the XY mode, the sagittal plane movement is displayed on the lefthand side of the screen 20 (vertical position on Y axis and anterior/posterior position on X axis), while frontal plane movement is displayed on the righthand side of the screen 20 (vertical position on Y axis and lateral position on X axis). In the sweep mode, the vertical, anterior/posterior, and lateral positions of the mandible are all displayed simultaneously as a function of time.

The velocity/frontal mode, indicated by lamp 32d, is always displayed in the X-Y mode. On the left side of the screen 20, the vertical position of the mandible is displayed along the Y axis, while the vertical velocity of the mandible is displayed along the X axis. On the right side of the screen 20, the vertical position of the mandible is displayed along the Y axis and the lateral position of the mandible is displayed along the X axis.

In the velocity/horizontal X-Y mode, indicated by lamp 32e, the vertical position of the mandible is displayed with respect to the vertical velocity of the mandible on the left side of the screen 20, while the anterior/posterior position of the mandible is displayed with respect to the lateral position of the mandible on the right side of the screen 20. The velocity-horizontal mode may also be displayed in a sweep display mode in which the vertical velocity of the mandible, the vertical, lateral and anterior/posterior positions of the mandible are simultaneously displayed with respect to time.

The MKG+ EMG mode, indicated by lamp 32f, utilizes only the sweep display mode. In this mode, the vertical, anterior/posterior, and lateral positions of the mandible, the vertical velocity of the mandible, and four channels of an electromyograph (not shown) are simultaneously displayed on the screen 20 with respect to time.

In the EMG (raw) mode, indicated by lamp 32g, four external channels are simultaneously displayed on the screen 20 with respect to time.

Finally, in the EMG (processed) mode, indicated by lamp 32h, four different external channels are simultaneously displayed on the screen 20 with respect to time.

When power is initially applied to the kinesiograph, the sagittal mode 32a is selected. Thereafter, other modes are selected by actuating selector switch 36 downwardly to select modes indicated by the lamps below 32a. Modes indicated by lamps above the lamps for the the current mode are selected by actuating switch 36 upwardly.

In operation, the real-time inputs from the kinesiograph are displayed on the screen 20 by closing a view switch 38. When a waveform is to be stored, a beam switch 40 is actuated to the "on" position and, thereafter, the stored waveform is continuously displayed. When the stored waveform is to be erased, an erase switch 42 is actuated. Finally, a tape switch 44 may be actuated to view externally generated kinesiograph signals, such as those recorded on magnetic tape or generated by a computer or analyzer. The cable 24 is terminated by a connector which plugs into a conventional jack 48 on the panel 30.

In the sweep display mode, the system may operate in an expand mode so that one-quarter of the displayed waveform extends across the entire screen 20. Accordingly, the selector knob 34 is actuated to the expand position, thereby displaying the first quarter of the waveform across the entire screen. The viewed portion is advanced one-eighth of the waveform (so that the portions between one-eighth and three-eighths of the waveform are displayed) by momentarily actuating pushbutton switch 46. Thereafter, the displayed portion is advanced one-eighth of the waveform by repetitively actuating the switch 46 until the first quarter of the waveform is once again displayed.

Figure 2A:
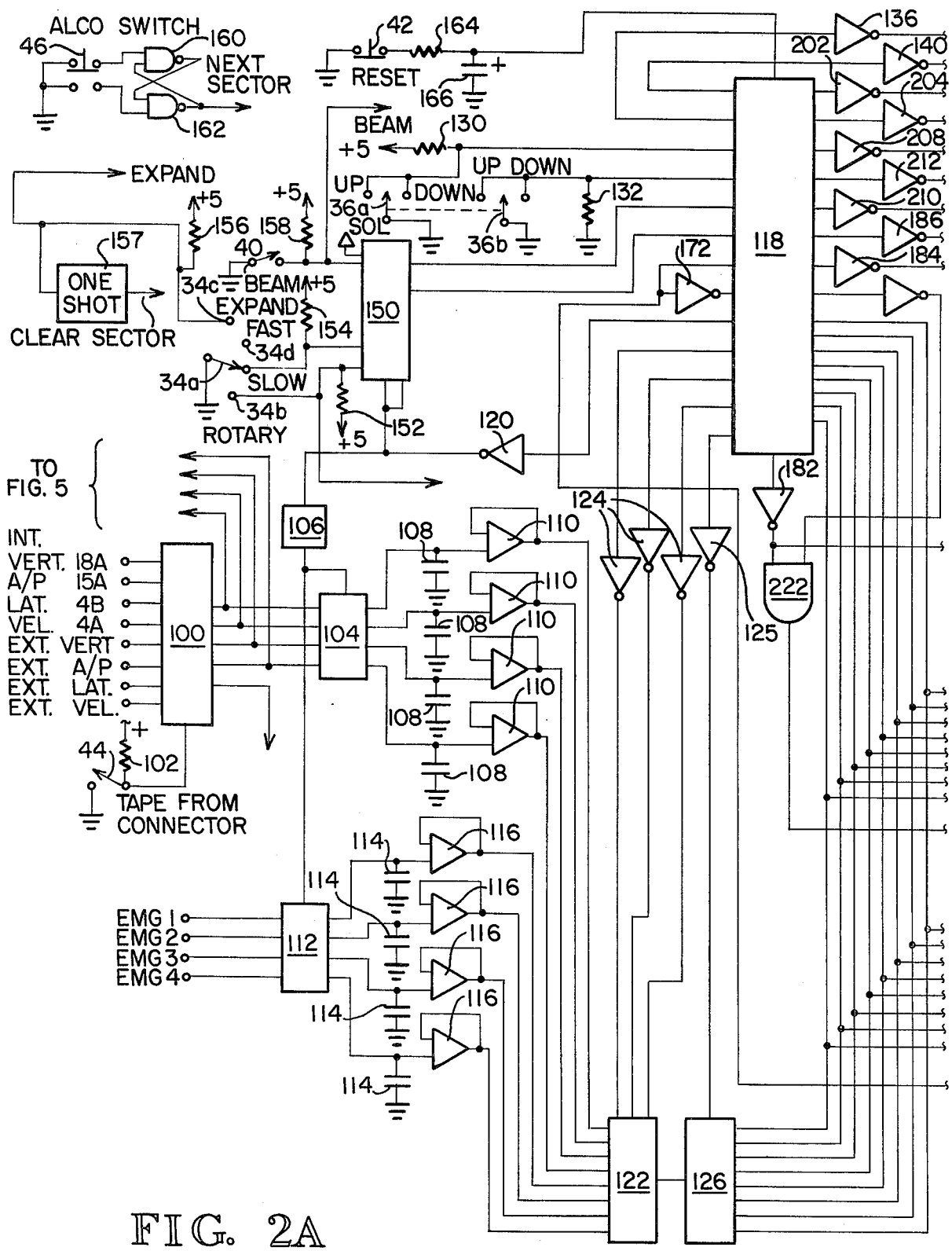
FIGS. 2A and 2B are a schematic of the display circuitry for digitizing the kinesiograph waveforms and the microprocessor for controlling the operation of the remaining circuitry.
Figure 2B:
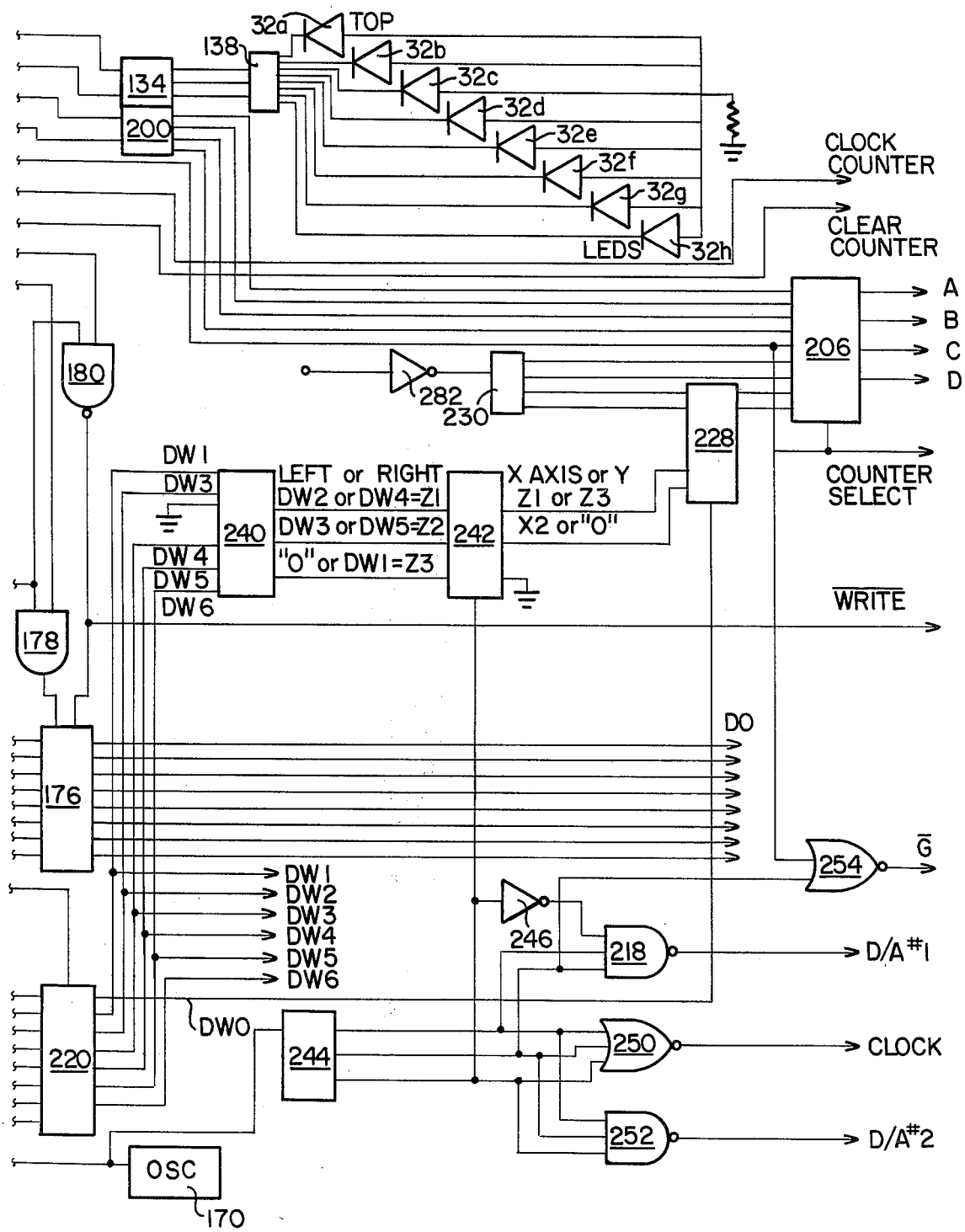

A schematic of the front end portion of the display system circuitry is illustrated in FIGS. 2A and 2B. The vertical, anterior/posterior, lateral, and velocity inputs are applied to a multiplexer 100 along with corresponding inputs from an external source through jack 48. The multiplexer 100 selects either the internal or the external inputs by either opening or closing the tape switch 44 to switch the control input to the multiplexer 100, which is normally held high through resistor 102.

The inputs selected by the multiplexer 100 are then applied to a sample switch 104 which samples the inputs when it is triggered by a pulse from one-shot 106. The inputs are thus connected to hold circuits during the sample period, each of which consists of a storage capacitor 108 and a voltage-follower operational amplifier 110. Similarly, the external electromyograph inputs are sampled by a four-pole switch 112 when triggered by the one-shot 106 to apply the EMG inputs to respective capacitors 114 and voltage-follower operational amplifiers 116. The capacitors 108,114 thus store samples of the real-time inputs, and the stored samples are continuously output by the operational amplifiers 110,116. The one-shot 106 actuating the fourpole switches 104,112 is periodically triggered by a conventional microprocessor 118 through inverter 120.

The stored samples from the operational amplifiers 110,116 are applied to a one-of-eight demultiplexer 122 which is controlled by the microprocessor 118 through inverters 124. The demultiplexer 122 sequentially selects each of the stored samples and applies it to an analog-to-digital converter 126 which generates a digital word indicative of the amplitude of the sample. The digital word is then applied to the data bus of the microprocessor 118. The microprocessor 118 thus periodically receives a digital indication of the amplitude of the real-time inputs at a sufficiently high rate to reconstruct the real-time inputs.

As mentioned above, the real-time inputs which are to be sampled are selected by the multiplexers 104,112 under control of the microprocessor 118 in accordance with the mode selected by actuating the switch 36 either up or down. The microprocessor 118 is automatically reset to the sagittal mode when power is applied to the system. As explained above, the mode switch contacts 36a,b are then repetitively opened or closed to switch to other modes. When the switch 36 is actuated in either its "up" or "down" position, switch contact 36a closes, thereby grounding an input to microprocessor 118, which is normally held high through resistor 130. The low applied to the input of the microprocessor 118 indicates that valid data is being applied to the microprocessor 118. When the switch 36 is actuated to its downward position, switch contact 36b closes, thereby grounding a data input to the microprocessor 118, which is normally held high through resistor 132 to indicate switching in one direction. Similarly, actuating the switch in the "up" position caues a valid data high to be applied to the data input to indicate switching in the other direction.

After the desired mode has been selected, the proper indicating lamp 32a-h is illuminated by the microprocessor 118. The microprocessor initially clears a counter 134 through inverter 136 so that the counter 134 generates a zero output. The zero output is applied to a decoder 138 which then illuminates the light-emitting diode 32a indicative of the sagittal mode. Thereafter, the clock 134 is incremented by the microprocessor 118 through inverter 140 to cause the counter 134 to apply a binary number of increasing magnitude to the decoder 138. The decoder 138 then sequentially illuminates LEDs 32 until the proper LED is illuminated. An upper light-emitting diode, i.e., 32b, is illuminated after a lower light-emitting, e.g., 32f, is illuminated by closing the "up" switch contact 36a. The microprocessor 118 then resets the clock 134 and applies a single pulse to the clock input of the counter 134.

The mode with which the system displays the selected real-time inputs is controlled by selector knob 34 (FIG. 1), as explained above. The selector knob 34 displaces a switch contact 34a to one of several switch contacts 34b-e. The switch contact 34a, being grounded, grounds a first input to a multiplexer 150, normally held high through resistor 152 when the selector 34 is in the X-Y position. Similarly, the switch contact 34a grounds a second input to the multiplexer 150 (which is normally held high through resistor 154) when the selector 34 is in the 1 sec/cm position. Neither of the aforementioned inputs to the multiplexer 150 are grounded when the selector 34 is in either the 0.1 sec/cm position or the expand position. Furthermore, in the expand position, an EXPAND signal, which is normally high through resistor 156, is held low.

The multiplexer 150 normally connects the contact 34c to a testable input of the microprocessor 118. However, when the microprocessor 118 triggers the one-shot 106 to sample the inputs, it also causes the multiplexer 150 to connect the contact 34b to the testable input. Accordingly, the microprocessor 118 periodically samples the switch contacts 34a,b to determine the position of the switch 34. If neither of the inputs are low, the switch 34 is determined to be in a 0.1 sec/cm condition in the regular or 0.025 sec/cm in the expanded mode.

In a similar manner, the microprocessor 118 detects a closing of the beam switch 40 by periodically testing an input normally held high through resistor 158 which is grounded by closing the beam switch 40.

As mentioned above, in the expand mode, the X axis of the waveform is expanded by a factor of 4 so that only one-quarter of the waveform is displayed on the screen 20. The particular quarter of the waveform that is displayed is advanced in one-eighth waveform increments by actuating the normally closed pushbutton switch 46. The switch 46, in its closed position, causes a low to be generated at the output of NAND-gate 160, which generates a high at the output of NAND-gate 162. Opening the switch 46 applies a low to the input of NAND-gate 162 to cause the output of NAND-gate 162 to go high to produce a NEXT SECTOR output. NAND-gates 160, 162 thus function as a flip-flop to eliminate bounce of the switch 46.

The erase switch 42 (FIG. 1), which is closed to erase the stored kinesiograph signals, applies a low through resistor 164 to the reset terminal of microprocessor 118, which is normally held high through an internal pull-up resistor. The microprocessor 118 is also reset upon initial "power up" through capacitor 166. Upon being reset, the microprocessor 118 erases the random access memory where the samples of the real-time inputs are stored. However, the microprocessor 118 must distinguish between a reset which occurs on "power up" and a reset which occurs when data is to be erased. As explained in greater detail hereinafter, after the microprocessor 118 has been initially reset upon "power up" a predetermined number stored in an internal read-only memory is written into a byte of an internal random access memory. Each time the microprocessor 118 is reset, it checks for the presence of this number. If the number is present, the reset is determined to be caused by closing the switch 42. If the predetermined number is not present, the reset is determined to be caused by an initial "power up."

The microprocessor 118 operates in a time sequence through clock pulses generated by an oscillator 170. Inverted clock pulses are also applied to the microprocessor 118 by inverter 172.

The microprocessor 118 periodically receives data words from analog-to-digital converter 126 indicative of the amplitude of the real-time input signals. It then calculates a digital value indicative of a position on the screen 20 which corresponds to the digital value and which has been offset to either side if the signal is to be displayed on either the right or left side of the screen. Thus a zero-volt sample in the X direction may be transformed to a zero-volt value where the samples are to be displayed on the right side of the screen (i.e., so a spot is placed in the center of the screen), and it may be transformed to a minus voltage value where the sample is to be stored on the left side of the screen.

The data words generated by the microprocessor 118 are applied to a tri-state latch and buffer 176 through the microprocessor data bus. The data on the bus is latched into buffer 176 by a low at the output of AND-gate 178. The data latched in buffer 176 is output to the RAM data bus by a low at the output of NAND-gate 180. The latch/buffer 176 can be operated in a variety of modes. Data can be simultaneously latched into buffer 176 and presented to the RAM data bus by generating a low at the output of inverter 182. Inverter 182 is "WRITE" for data bus. This may not be set low. It goes low when we write data from microprocessor 118 to data bus. Whenever data is presented to the RAM data bus at the output of NAND-gate 180, a negative-going WRITE signal is also produced to write the data on the RAM data bus into the random access memories.

The microprocessor 118 not only determines the data word which is to be written into the random access memory, but it also determines the address in which the data is to be written. To understand the memory addressing function, it is necessary to be understand how data is stored in memory. Basically, the memory contains 16k bytes arranged in 4k blocks. The first 4k bytes store the samples indicative of the vertical position of the mandible, the second 4k bytes store the samples indicative of the anterior/posterior position of the mandible, the third 4k bytes of the memory store the samples indicative of the lateral position of the mandible, and the final 4k bytes of memory store the samples indicative of the vertical velocity of the mandible. In the sweep mode, data is read out of memory in sequence so that when all four stored inputs are being displayed, all of the vertical sample points are first read, then all of the anterior/posterior samples, then all of the lateral samples, and finally, all of the vertical velocity samples. In the X-Y mode, however, the sample points for the inputs, which are displayed with respect to each other, are alternately read from memory. Thus, in the sagittal/frontal mode, the first sample of the vertical signal is first read from memory, followed, in sequence, by the first a/p sample, the second vertical sample, second a/p sample, third vertical sample, third a/p sample . . . nth vertical sample, nth a/p sample, first lateral sample, first vertical sample, second lateral sample, second vertical sample . . . nth lateral sample, nth vertical sample.

After real-time samples are digitized by the A/D converter 126 and processed by the microprocessor 118, they are stored in memory in the sequence at which they occur. The particular 1k byte in which data is to be stored is generated by a counter 200 which is initially cleared through inverter 202. Thereafter, as each 1k byte of memory is filled, the counter 200 is incremented through inverter 204 to increment the binary address at the output of counter 200. The address is then routed through a multiplexer 206 by the counter-select output going high through inverter 208. Thus, when data is to be written into memory, the counter-select output goes high and the particular 1k byte of memory in which the data is to be read appears on the A,B,C,D outputs. As explained in greater detail hereinafter, the particular byte within that 1k block is selected by a counter which is initially cleared by a CLEAR COUNTER pulse through inverter 210 and subsequently incremented through inverter 212.

The A-D address outputs also select the proper byte of memory from which data is to be read. However, the readout address is generated in a different manner, as explained hereinafter, and is routed through the multiplexer 206 by a low COUNTER SELECT signal. The reason for the different addressing circuitry is that the order in which data is read from memory depends upon the particular display mode selected. A display word indicative of the display mode is generated by the microprocessor 118 on its data bus and stored in a latch 220 when the output of AND-gate 222 goes low. The DW0 bit of the display word indicates whether the display system is in the sweep or the X-Y mode. In the sweep mode, the DW0 bit is high, which causes a multiplexer 228 to apply the most significant two bits of a counter 230 to the multiplexer 206. The high order bits of the counter 230 are applied directly to the multiplexer 206. Insofar as COUNTER SELECT is low when data is to be read from the memory, the multiplexer 206 thus applies the outputs of counter 230 to the A-D address outputs in order to select one of the 1k byte blocks from which data is to be read. The counter 230 is clocked once every time the memory address is to be incremented to the next 1k byte block through inverter 232, as explained in greater detail hereinafter. Thus, in the sweep mode, the 1k byte block selection is accomplished in a relatively straightforward manner. This relative simplicity stems from the sequential readout of data in the sweep mode, as explained above.

In the X-Y mode, the readout order is more complex and, accordingly, so is the addressing scheme. In the X-Y mode, the DW1-5 bits of the data word are used to select the 1k byte block being addressed. The first bit DW1 of the display word indicates what kinesiograph input is being displayed on the Y axis of the right side of the screen 20. If DW1 is low, the vertical position of the mandible is displayed along the Y axis on the right side of the screen 20. If DW1 is high, the anterior/posterior position of the mandible is displayed along the Y axis on the right side of the screen 20. The Y axis on the left side of the screen 20 always displays the vertical position of the mandible so that it is not necessary to provide a data word bit for the Y axis on the left side of the screen.

The second and third bits of the data word, DW2 and DW3, indicate what is displayed along the X axis on the right side of the screen 20. It will be remembered that the kinesiograph samples are stored in 4k byte blocks, with the vertical position samples being stored in the first 4k byte block, the a/p position samples being stored in the second 4k byte block, the lateral position samples being stored in the third 4k byte block, and the vertical velocity samples being stored in the fourth 4k byte block. The DW3 and DW2 bits of the data word select which memory block—and hence which set of position samples—are to be displayed along the X axis on the right side of the screen. Accordingly, DW3,DW2 are "0,0" (binary zero) when the stored samples indicative of the vertical of the mandible are to be displayed along the X axis on the right side of the screen 20. Similarly, DW3,DW2 are "0,1" (binary one) when the anterior/posterior position is to be displayed, "1,0" (binary two) when the lateral position of the mandible is to be displayed, and "1,1" (binary three) when the vertical velocity of the mandible is to be displayed.

The data word bits DW4 and DW5 select the 4k byte blocks in the same manner as explained above with respect to DW2 and DW3 to indicate what samples are to be displayed along the X axis on the left side of the screen 20.

The final display word bit, DW6, is used to offset real-time kinesiograph signals on the screen 20 so that they will have a position corresponding to the stored kineosiograph samples which have been offset by the microprocessor 118 to place them on either the left or right side of the screen. This circuitry is explained in greater detail hereinafter.

As mentioned above, counter 230 is incremented once after every one thousand bytes of memory have been accessed. The third bit at the output of the counter 230 thus changes state after every four thousand bytes of memory have been accessed. Thus the control input to multiplexer 240 switches every 4k bytes. During the first 4k bytes of memory (when the control input to multiplexer 240 is low), the memory is accessed to read data which will be displayed on the lefthand side of the screen 20 and the upper three inputs are applied to the correspondingly positioned outputs. When the control input to multiplexer 240 is high, the memory is accessed for data which is displayed on the righthand side of the screen 20, and the three lower inputs are applied to correspondingly positioned outputs.

The outputs of multiplexer 240 are applied to three inputs of multiplexer 242. The control input of multiplexer 242 receives clock pulses from the oscillator 170 which have been divided by counter 244. The control input to multiplexer 242 determines whether the memory is being accessed to receive samples which are to be displayed in either the X or Y axes of the screen 20. When the samples are to be displayed along the X axis, the upper two inputs to the multiplexer 242 are connected to the correspondingly positioned outputs and, through multiplexer 206, to the most significant two bits of the memory block address C and D. When the memory is being accessed to display samples along the Y axis of the screen 20, the lower two inputs of the multiplexer 242 are connected to correspondingly positioned outputs of the multiplexer 242. The outputs of multiplexer 242 are connected to the most significant bits of the outputs of multiplexer 206 to select the 4k byte block, in which samples of specific kinesiograph inputs are stored. Thus, for example, when the memory is accessed to display samples along the Y axis, the high-order address bit D is at ground because of the grounded lower input to multiplexer 242. At the same time, the lower order bit C is connected to the ground at the input to multiplexer 240 for a display on the lefthand side of the screen and to the DW1 bit when data is being displayed on the righthand side of the screen. As a result, the two highest order address bits being accessed to display samples along the Y axis on the lefthand side of the screen are "00." This selects the first 4k byte block of memory, where, it will be remembered, the vertical position samples are stored since the vertical mandibular position is always displayed along the X axis on the lefthand side of the screen 20. On the righthand side of the screen 20, the Y axis represents either the vertical position of the mandible or the anterior/posterior position of the mandible. The two high-order bits of address when samples are being displayed along the Y axis of the right side are "0" and DW1. If DW1 is "0," the high-order address bits are "00," thus selecting the first 4k byte block in which vertical position samples are stored. If DW1 is "1," the high-order address bits are "01," which selects the second 4k byte block of memory, in which the anterior/posterior position samples are stored. Similarly, when samples are to be displayed along the X axis on the lefthand side of the screen, the D and C address bits are equal to DW3 and DW2, respectively. As DW3 and DW2 can each be either "1" or "0," the stored samples for any of the kinesiograph inputs can be displayed along the X axis. When stored samples are to be displayed along the X axis on the righthand side of the screen 20, the D and C address bits are equal to the DW5 and DW4, respectively, which also can select any 4k byte block of memory.

The divided clock pulses at the output of counter 244 are also applied to a coding circuit consisting of inverter 246, NAND-gate 248, NOR-gate 250, and NAND-gate 252. The NAND-gate 248 decodes the three count of counter 244 to generate a D/A#1 pulse. NAND-gate 252 decodes the number seven count of counter 244 to generate a D/A#2 pulse. Finally, NOR-gate 250 decodes the zero count of counter 244 to generate a CLOCK #2 pulse which drives the memory-address generating circuitry, as explained in greater detail hereinafter. Finally, NOR-gate 254 is used to provide a relatively short duration pulse when COUNTER SELECT is low for use by the memory and addressing circuitry explained in greater detail hereinafter.

Figure 3A:
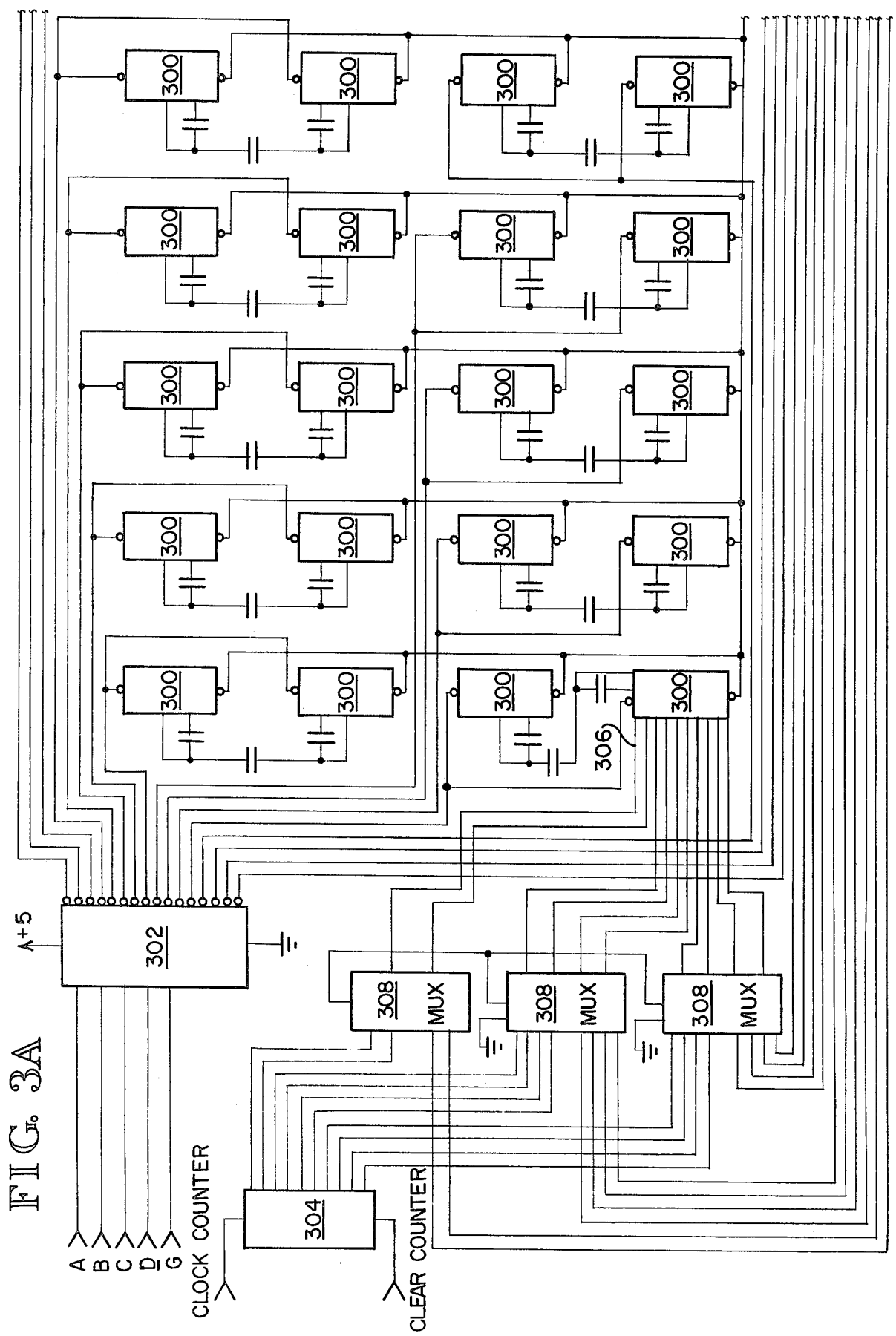
FIGS. 3A and 3B are a schematic of the memory and addressing circuitry.
Figure 3B:
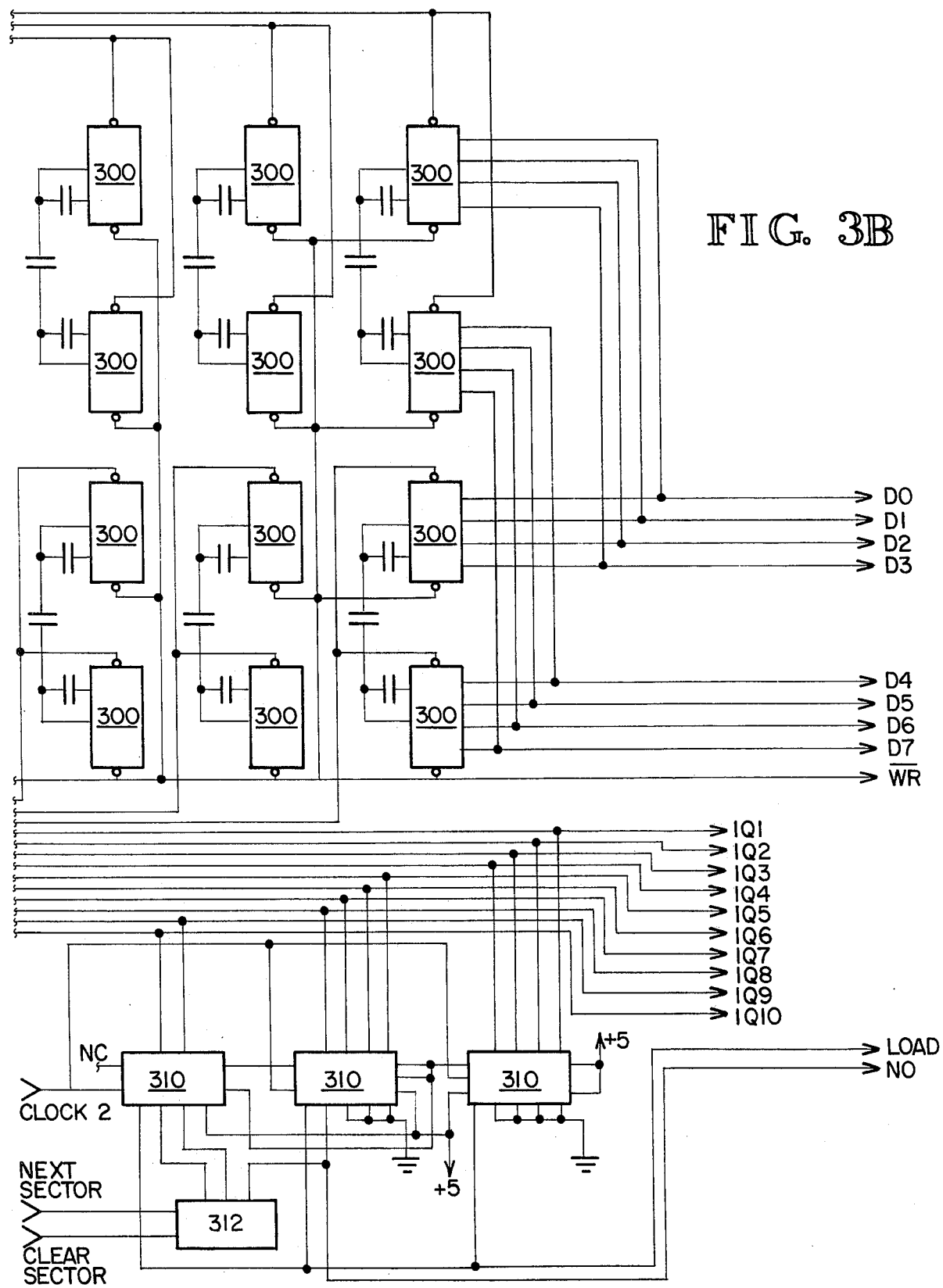

The memory and addressing circuitry illustrated in FIGS. 3A and 3B writes and reads data from the proper location in a bank of random access memories 300, each of which stores one thousand 4-bit bytes of data. The memories 300 are accessed in pairs to obtain an 8bit byte. Each pair of memories 300 is accessed by a chip-select signal generated from the highorder address bits A,B,C,D by a chip-select decoder 302. The chip-select decoder 302 is enabled by the timing pulse G from NOR-gate 254 (FIG. 2B). Consequently, the memories 300 are accessed only when a WRITE pulse is produced when data is to be stored in memory 300 or on the zero count of counter 244 when neither of two digital-to-analog converters, described hereinafter, are active. The particular byte in each pair of memories 300 which is being accessed is determined differently, depending upon whether data is being written into memory or read out of memory.

When data is being written into memory, a counter 304 is initially cleared by the microprocessor through inverter 210 (FIG. 2A), as explained above. The microprocessor 118 then sequentially increments the counter 304 through inverter 212. The outputs of counter 304 are applied to a memory address bus 306 through multiplexers 308 since the COUNTER SELECT signal is high when data is to be written into memory 300.

When data is to be read from memory 300, the memory is addressed by programmable counters 310 having outputs which are connected to the address bus 306 by the multiplexers 308, COUNTER SELECT being low during data readout. The binary output IQ10-IQ1 of the counters 310 normally starts at zero and increments up to one thousand. At this time, IQ8 goes high to increment counter 230 (FIG. 2B) and the count resumes from zero once again. However, in the expand mode, the counters 310 are preset with an address generated by a counter 312 which is cleared by a CLEAR SECTOR pulse generated by one-shot 157 when the display mode selector 34 is initially moved to the expand position. Thereafter, the counter 312 is incremented by actuating the pushbutton switch 46 to generate a NEXT SECTOR pulse. The output of counter 312 is loaded into the counters 310 by a LOAD pulse generated by the display circuitry explained in greater detail hereinafter. Thus the counters 310 are initially loaded with the first memory address. But after later occurring portions of the displayed waveform are selected, the counters 310 are loaded with the memory address corresponding to the start of that portion of the waveform. For example, where the third quarter of the waveform is to be viewed, the counters 310 are preset to memory address 500 and thereafter increment to memory address 750, at which time a load pulse is once again generated to reload the counters 310. The low-order bit of the counter 312 is output as an N0 signal to indicate which portion of the waveform is being selected. The N0 output is low whenever the displayed waveform starts at an even quarter of the waveform, but is high whenever the displayed waveform starts between even quarter intervals of the waveform. As explained in greater detail hereinafter, the lower order readout address bits IQ1-IQ8 which are used to generate the sweep ramp increment from zero at the start of each quarter sweep. At the end of each quarter sweep, they are reset to zero. Using these address bits to sweep between one-eighth and three-eighths points on the waveform would cause the sweep to start in the middle of the screen, sweep to the end, start sweeping at the left edge, and then continue to the middle. Yet the data being read out would presume a continuous sweep from the left edge to the right edge. As a result, the manner in which the address bits generate the sweep must be altered when sweeping between odd multiples of one-eighth waveform.

Figure 4:
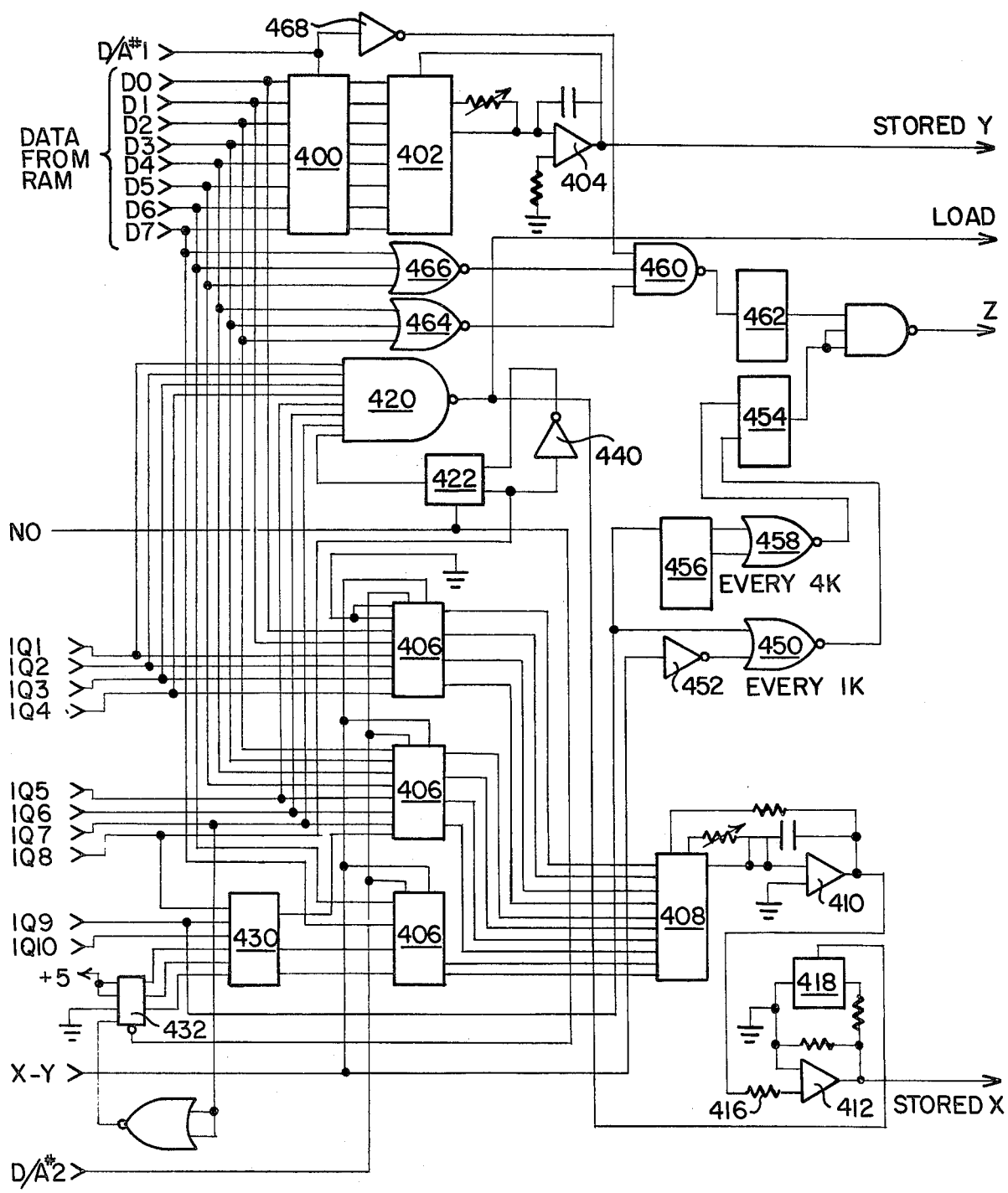
FIG. 4 is a schematic of the output circuitry for the digitized samples.

The output circuitry for the stored signals is illustrated in FIG. 4. Data from memory is applied to an eight-bit latch 400 when a D/A#1 pulse is produced by NAND-gate 248 (FIG. 2B). The output of latch 400 is applied to a digital-to-analog converter 402 which, in combination with operational amplifier 404, generates an analog signal having an amplitude corresponding to the digital value of the signal on the data bus. The output of the amplifier 518 indirectly drives the Y axis of the oscilloscope forming part of the display system.

The data on the data bus is also used to generate an analog signal for modulating the X axis of the oscilloscope in the X-Y mode. Accordingly, the data on the data bus is stored in the multiplexers 406 by the D/A#2 pulse generated by NAND-gate 252 (FIG. 2B) if the X-Y input is low, which will be the case in the X-Y mode when the selector knob 34 is in the X-Y position. Data from the data bus is then applied to a second digital-to-analog converter 408, which, in combination with operational amplifier 410, generates an analog signal at the output of amplifier 410 having an amplitude corresponding to the binary signal on the data bus. This signal is applied to a stored X output through operational amplifier 412, having a gain equal to the ratio of resistor 414 to the resistance of resistor 416 since switch 418 is then open.

In the sweep mode, the multiplexer latches 406 store the memory address from the counters 310 (FIG. 3B) and generate an analog signal on the stored X output proportional thereto. It will be remembered that in the sweep mode, the memory address starts at zero and increments to one thousand. Accordingly, the analog signal at the output of amplifier 412 starts at zero volts and rises linearly to a predetermined voltage.

The one thousand-bit memory address from counters 310 is decoded by a NAND-gate 420, assuming for the moment that multiplexer 422 applies IQ8 to the input of NAND-gate 420. NAND-gate 420 then generates a LOAD pulse which, as explained above, resets the counters 310 to zero. Consequently, the analog signal at the stored X output once again begins rising from zero.

In the expand mode, the manner in which the memory address generates the sweep ramp must be modified, as explained above, since the memory addressing does not start at the first memory address nor does it continue to the last memory address. Instead, only one-quarter of the address locations are accessed each sweep. Consequently, in the expand mode, multiplexer 430 applies the output of a counter 432 to the digital-to-analog converter 408 through multiplexer 406. The preset output of counter 432 is a binary value corresponding to a predetermined negative voltage which causes the sweep to start on the lefthand side of the screen 20 regardless of the actual memory address at the start of the sweep. Thereafter, the IQ1 through IQ7 address bits applied to the digital-to-analog converter 408 begin incrementing for the next two hundred fifty memory addresses. IQ8 then goes high, causing the output of NAND-gate 420 to go low, thereby once again presetting the counters 310 (FIG. 3B) to the proper memory address and applying the output of counter 432 to the digital-to-analog converter 408.

The above-described operation for generating a sweep in the expand mode is satisfactory when the sweep begins at even quarter intervals of the displayed waveform. This is because the binary number on the IQ1 through IQ8 bits of the memory address increment from zero to two hundred fifty during this time period. However, as explained earlier, where the start of the displayed waveform begins at odd multiples of one-eighth of the waveform, the address IQ1-IQ8 increments from one hundred twenty-five to two hundred fifty, is then reset to zero, and then increments to one hundred twenty-five. If the stored X waveform was then generated directly from the address, the waveform would be displayed from the center of the screen to the right and then from the left edge of the screen to the center. Consequently, when the sweep is to begin at odd multiples of one-eighth of the waveform, the N0 signal generated by counter 312 (FIG. 3B) switches multiplexer 422 so that IQ8 generated by inverter 440 is applied to the NAND-gate 420. NAND-gate 420 is then reset at the one hundred twenty-eight count so that the sweep begins at that point.

The Z axis of the oscilloscope is modulated to blank the display under certain circumstances. Basically, the display is blanked whenever data is substantially zero and the digital-to-analog converter 408 is active, or after every one thousand bytes of memory have been accessed in the sweep mode and the sweep is retracing, or after every four thousand bytes of memory have been accessed in the X-Y mode and a new set of samples are to be displayed. Accordingly, NOR-gate 450 is enabled through inverter 452 whenever the selector knob 34 is not in the X-Y mode. Insofar as IQ10 changes state after every one thousand bytes have been accessed, a pulse is generated at the output of NOR-gate 450 every one thousand bytes, which triggers one-shot 454. Similarly, the pulses occurring after every 1k bytes increment counter 456. The binary three output (11) of counter 456 is decoded by NOR-gate 458 to trigger the one-shot 454 after every four thousand bytes of memory have been accessed. Similarly, NAND-gate 460 triggers one-shot 462 to also generate a blanking pulse under appropriate circumstances. NAND-gate 460 triggers one-shot 462 if all of the data bits are found to be low by NOR-gates 464,466 during the D/A#1 one pulse through inverter 468 if the memory address is not at one thousand twenty-eight, as decoded by NAND-gate 420.

Figure 5:
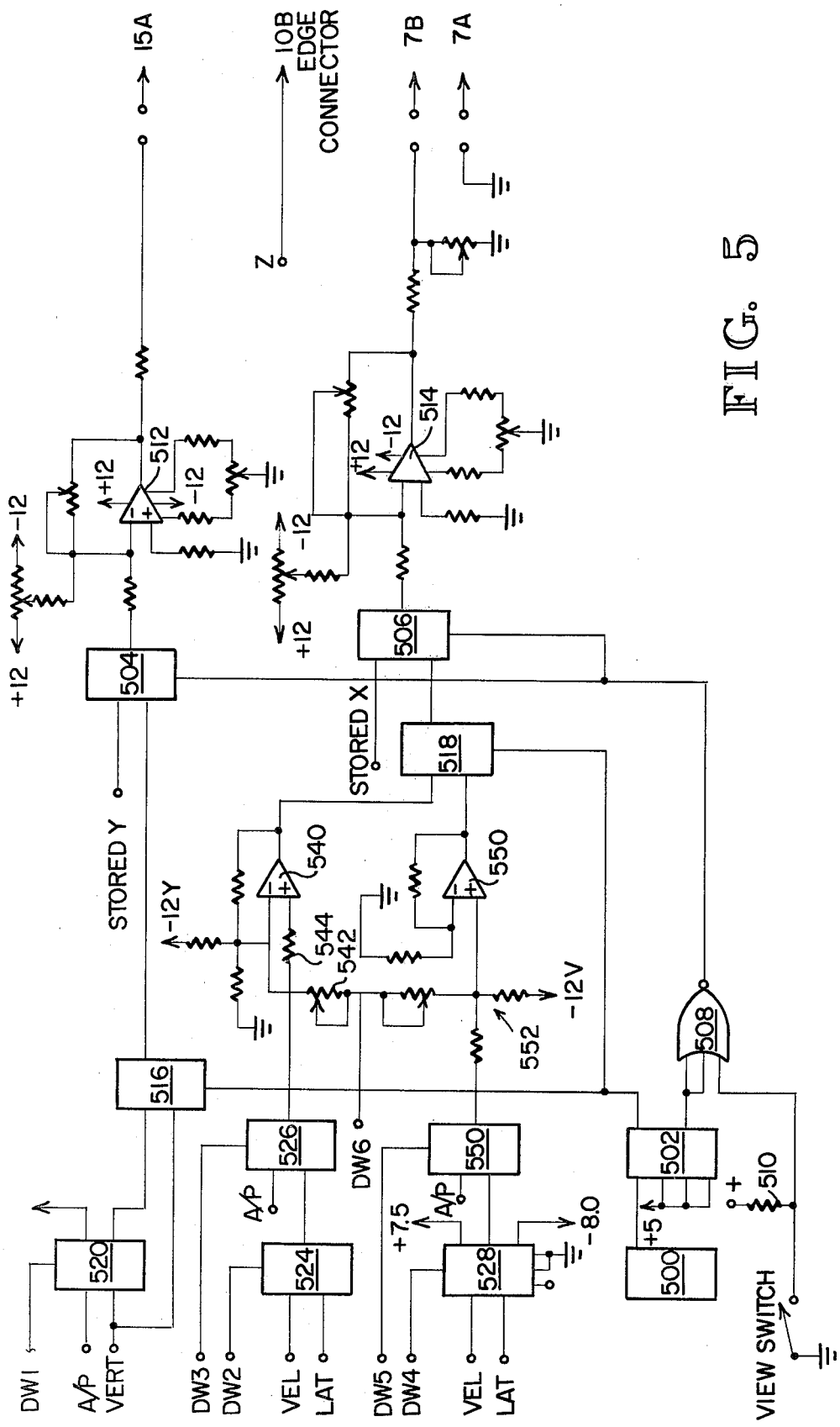
FIG. 5 is a schematic of view circuitry for combining the stored kinesiograph signals with the corresponding real-time kinesiograph signals.

The stored Y and X outputs from amplifiers 404, 412, respectively, are applied to a view circuit, illustrated in FIG. 5. Basically, the view circuit combines the stored signals to be displayed with corresponding real-time signals from the kinesiograph and positions the signals at the proper location on the screen 20. The view circuitry utilizes a chopping display mode from a pulse train generated by an oscillator 500. The output of the oscillator 500 is applied to a counter 502 which generates a pair of reduced frequency clocks, one of which is twice as fast as the other. The lower frequency signal is applied to respective control inputs of multiplexers 504,506 through NOR-gate 508 when NOR-gate 508 is enabled by closing the view switch 38. When view switch 38 is open, NOR-gate 508 is disabled through resistor 510. Disabling NOR-gate 508 holds the output low, thereby causing multiplexer 504 to continuously connect the stored Y output of amplifier 404 (FIG. 4) to the input of amplifier 512 and causing multiplexer 506 to continuously connect the stored X output of amplifier 412 to amplifier 514. Enabling NOR-gate 508, however, causes the multiplexers 504,506 to alternately switch between the stored Y and stored X outputs, respectively, and the outputs of respective multiplexers 516,518. The control inputs of multiplexers 516,518 receive the higher frequency clock pulses from counter 502.

Multiplexer 516 receives the real-time vertical signals from the kinesiograph as well as the output from still another multiplexer 520. The control input of multiplexer 520 receives the first bit DW1 of the display word to select either the anterior/posterior or vertical inputs from the kinesiograph. The multiplexer 516 alternately applies the kinesiograph signals to the multiplexer 504 that are to be displayed on the left and right-hand side of the screen. Multiplexer 516 always applies the vertical kinesiograph signals to the multiplexer 504 when the control input to multiplexer 516 is low because the vertical kinesiograph signal is always displayed along the Y axis on the lefthand side of the screen. However, either the anterior/posterior or vertical kinesiograph signals are displayed along the Y axis of the righthand side of the screen. Consequently, if DW1 is low, multiplexer 520 applies the vertical kinesiograph signal to the other input of multiplexer 516 so that multiplexer 516 continuously outputs the vertical kinesiograph signal. If DW1 is high, the multiplexer 516 alternately outputs the vertical and anterior/posterior kinesiograph signals so that they are displayed on the left and righthand side of the screens, respectively.

The circuitry for selecting the input to be displayed on the X axis is derived in a similar manner. The velocity and lateral kinesiograph signals are applied to a multiplexer 524 which selects either the velocity or lateral kinesiograph inputs for display along the X axis at the left side of the screen, assuming that DW3 is zero. If DW3 is one, multiplexer 526 outputs the a/p signal. Thus if DW3, DW2 are "01," the real-time a/p kinesiograph signal is displayed along the X axis on the left side of the screen. If the display word bits are "10," the real-time lateral kinesiograph signal is displayed along the X axis on the lefthand side of the screen; and if they are "11," the real-time velocity kinesiograph signal is displayed along the X axis on the lefthand side of the screen.

In a similar manner, multiplexers 528,530 select the real-time kinesiograph signal to be displayed along the X axis on the righthand side of the screen. Thus, for "DW5, DW4" equal to "01," the a/p real-time kinesiograph signal is displayed; "10," the lateral real-time kinesiograph signal is displayed; and "11," the real-time velocity kinesiograph signal is displayed along the X axis on the righthand side of the screen.

A zero-volt input to amplifier 512,514 would place a spot at the center of the oscilloscope screen. The stored Y and stored X signals have been mathematically offset by the microprocessor so that they have the proper voltages for displaying the signals on either the lefthand or righthand side of the screen. Thus a zero-volt X signal to be displayed on the lefthand side of the screen would actually be applied to amplifier 514 as a negative voltage. However, the real-time kinesiograph signals are not received with the proper offset. Accordingly, when the DW6 bit of the display word is high, a positive voltage is applied to the summing junction of amplifier 540 through potentiometer 542 which offsets the left side X output applied to amplifier 540 through resistor 544 and the proper amount so that zero volts at the output of multiplexer 526 generate a negative voltage at the output of amplifier 540. Similarly, the output of multiplexer 530 is offset with a positive voltage by amplifier 550 and resistors indicated generally at 552. In the sweep mode, of course, the offset is not required, so the DW6 is low. The outputs of amplifiers 512,514 are applied to the Y and X terminals of the conventional oscilloscope forming part of the kinesiograph.

Figure 6A:
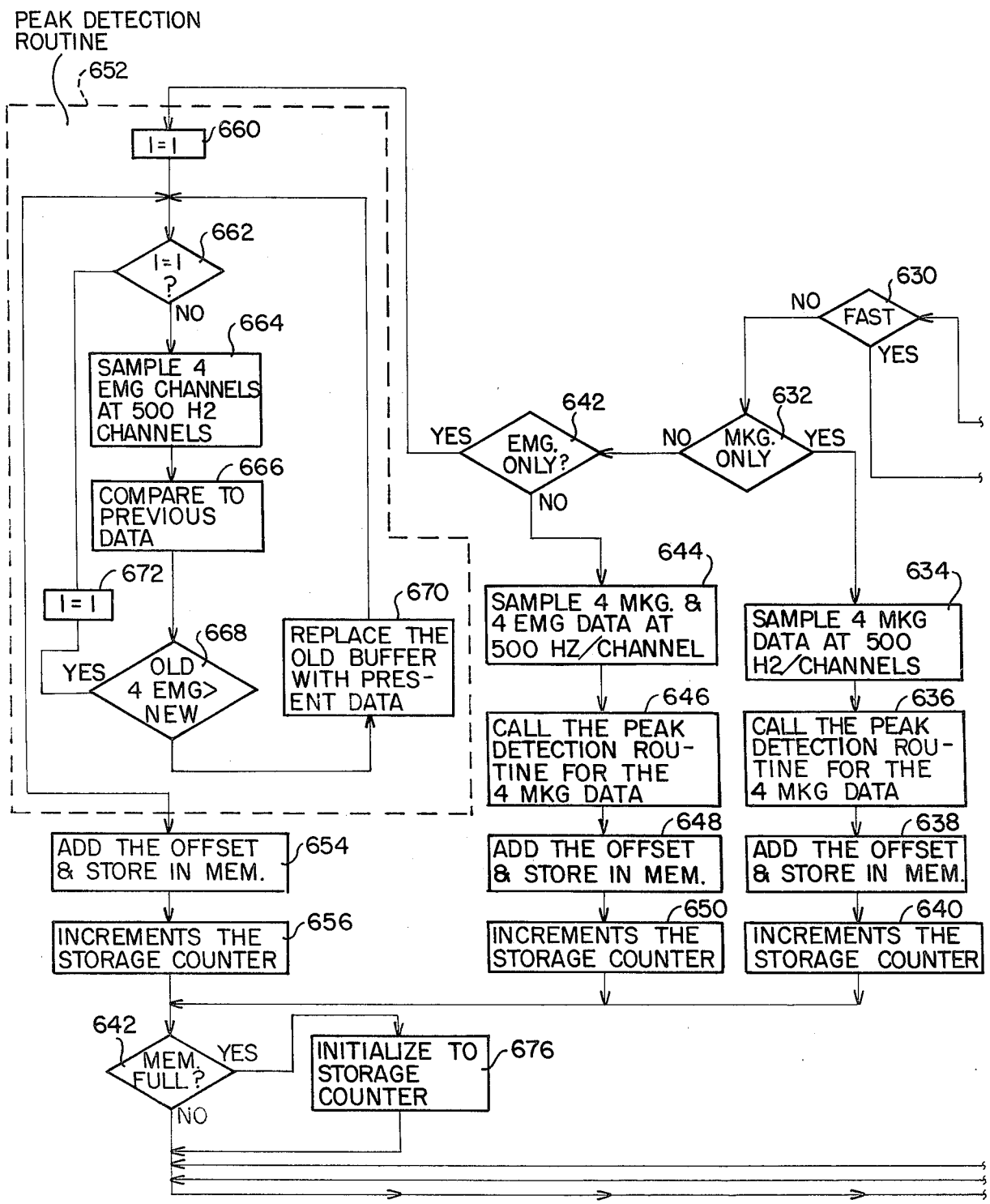
FIGS. 6A and 6B are a flow chart of the software controlling the operation of the microprocessor used in the storage and display device.
Figure 6B:
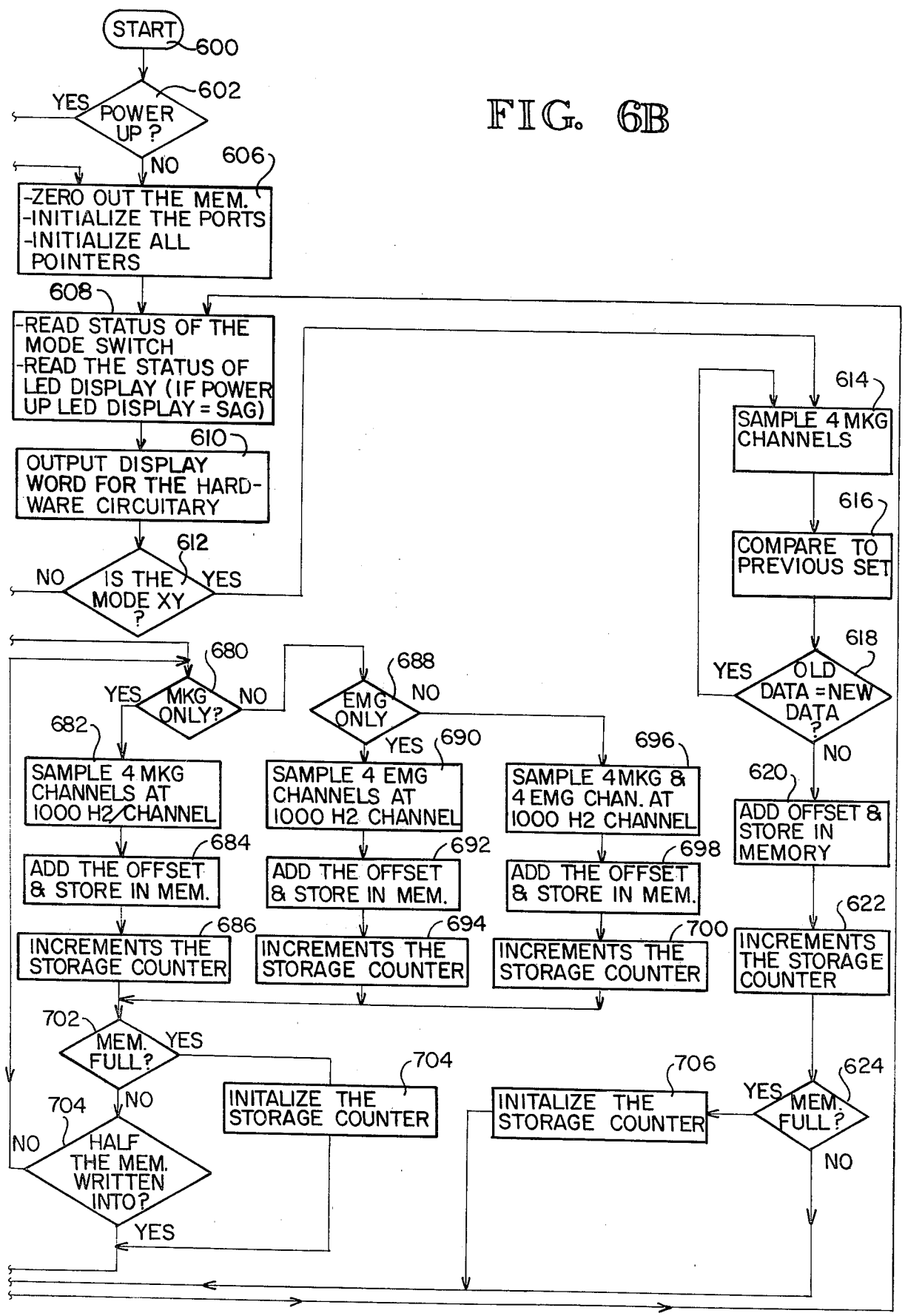

A software program for controlling the operation of the microprocessor 118 is illustrated in FIGS. 6A and 6B. The program starts at 600 when the microprocessor 118 is reset by either closing reset switch 42 (FIG. 2A) or upon initial "power up." The program determines the cause of the reset at 602. If the reset is caused by power being initially applied to the system, a number of parameters for the sagittal mode are set at 604 and the program then progresses to 606. If the reset is caused by closing switch 42, the program branches directly to 606.

At 606, the memory 300 (FIGS. 3A and 3B) is cleared, the I/O ports of the microprocessor 118 are initialized and all internal pointers of the microprocessor 118 are initialized. The program then progresses to 608, where the status of the mode switch 34 is read, the status of the LED indicators 32 is read to determine which kinesiograph waveforms are to be displayed. The microprocessor 118 then outputs a display word at 610 corresponding to the kinesiograph waveforms to be displayed.

The program then determines at 612 whether the system is in either the X-Y mode or the sweep mode. If the system is in the X-Y mode, the program branches to 614, where four MKG channels are sampled by the sample switch 104 and their digital values are read from analog-to-digital converter 126. These samples are compared to the previous set of samples at 616, and, if the current data and previous data are found to be identical at 618, the program loops back to 614. Otherwise, the program progresses to 620. The purpose of the "old data equals new data" determination at 618 is to prevent the memory 300 from being filled with identical values when the samples are not changing. This maximizes the storage efficiency of the memory.

The microprocessor 118 calculates an offset at 620 to place the sample at the desired position on the display screen. For example, a zero-value X signal requires a zero-volt signal applied to the X axis of the oscilloscope when the sample is to be displayed on the right side of the screen. However, the sample zero-volt value requires a negative voltage applied to the X axis of the display when the waveform is to be displayed on the left-hand side of the screen. After the offset has been added at 620, the storage counters 308 are incremented at 622 and, if the memory is found at 624 to have unused space, the program returns to 608. Otherwise, the storage counter is initialized at 626 before returning to 608. The program thus successively branches through 614-626 a large number of times to record a sufficient number of data points to show mandibular movement on the display screen.

If the system is found at 612 to not be in the X-Y mode, it is, of necessity, in the sweep mode. Accordingly, the program determines at 630 whether the system is in the fast or slow sweep modes. Assuming that the mode switch 64 is in the slow sweep position, the program determines at 632 whether only MKG (kinesiograph) inputs are present. Assuming that such is the case, the MKG inputs are sampled at 634 (as explained above with reference to 614), a peak detection subroutine is called at 636, and an offset is added to the sample at 638 for the same reason as discussed above with reference to step 620. Finally, the storage counter 308 (FIG. 3) is incremented at 640 and the program branches decision block 642.

In the event that additional signals besides MKG (kinesiograph) signals are being applied to the system, the program branches to 642 to determine if EMG (electromyograph) signals are present alone or in addition to MKG signals. If both EMG and MKG signals are being applied to the system, four MKG and four EMG inputs are sampled at 644, the peak detection subroutine of 646 is called in the same manner as in step 636, and an offset is added at 648 in the same manner as in 638. Finally, the storage counter 650 is incremented before progressing to decision block 642.

In the event that only EMG signals are found to be present at 642, the peak detection subroutine is called at 652, an appropriate offset is added and the resulting signal stored in memory at 654, and the storage counter is incremented at 656.

The peak detection subroutine called at 636, 646 and 652 first initializes a pointer at 660 and tests for the value of the pointer equal to five at 662. Four EMG channels are then sampled at 664 at a 500 Khz rate and the samples are compared to the previous samples at 666 before branching to decision block 668. If the old samples have a lower value than the new samples, the samples are increasing in value, thus indicating that the peak has not been reached. Accordingly, old samples are replaced in an internal buffer wih the new samples at 670, and the program returns to 662. If the old samples are larger than the new samples, thus indicating that the peak has been reached, the flag is incremented at 672. If the old samples are greater than the new samples for five successive loops, the "I=5" condition is detected at 662, causing the program to branch to 654. At this time, the samples in the buffer 670 are indicative of the peak values of the EMG signals.

Regardless of which path is taken, the program branches to 642, where the condition of the memory is checked. As long as the memory is not full, the program returns to 608. However, when the memory 300 becomes full, the storage counter 308 is initialized at 676 before returning to 608.

Returning now to decision block 630, if the mode switch 34 is found to be in the fast sweep mode, the program branches to 680, where the characteristic of the inputs is determined. If only MKG (kinesiograph) signals are present, the MKG's inputs are sampled at 682, the offset is added and the result stored in memory 684, and the storage counter is incremented at 686. In the event that the incoming signals are not MKG signals only, the program branches to 688 to determine whether only EMG signals are present. If such is the case, the EMG inputs are sampled at 690, the offset is added to the samples and the result stored in memory at 692, and the storage counter is incremented at 694. Finally, if the incoming signals are found to consist of both MKG and EMG data, four MKG and four EMG channels are sampled at 696, an offset is added to the samples and the result stored in memory at 698, and the storage counter is incremented at 700.

Regardless of which path the program follows, the available capacity of the memory is checked at 702 and, if additional space is available, the program determines at 704 whether half of the memory has been filled. If so, the program branches to 608. Otherwise, the program returns to 680. If the memory is found to be full at 702, the storage counter is initialized at 706 before returning to 608.

Figures 7, 8:
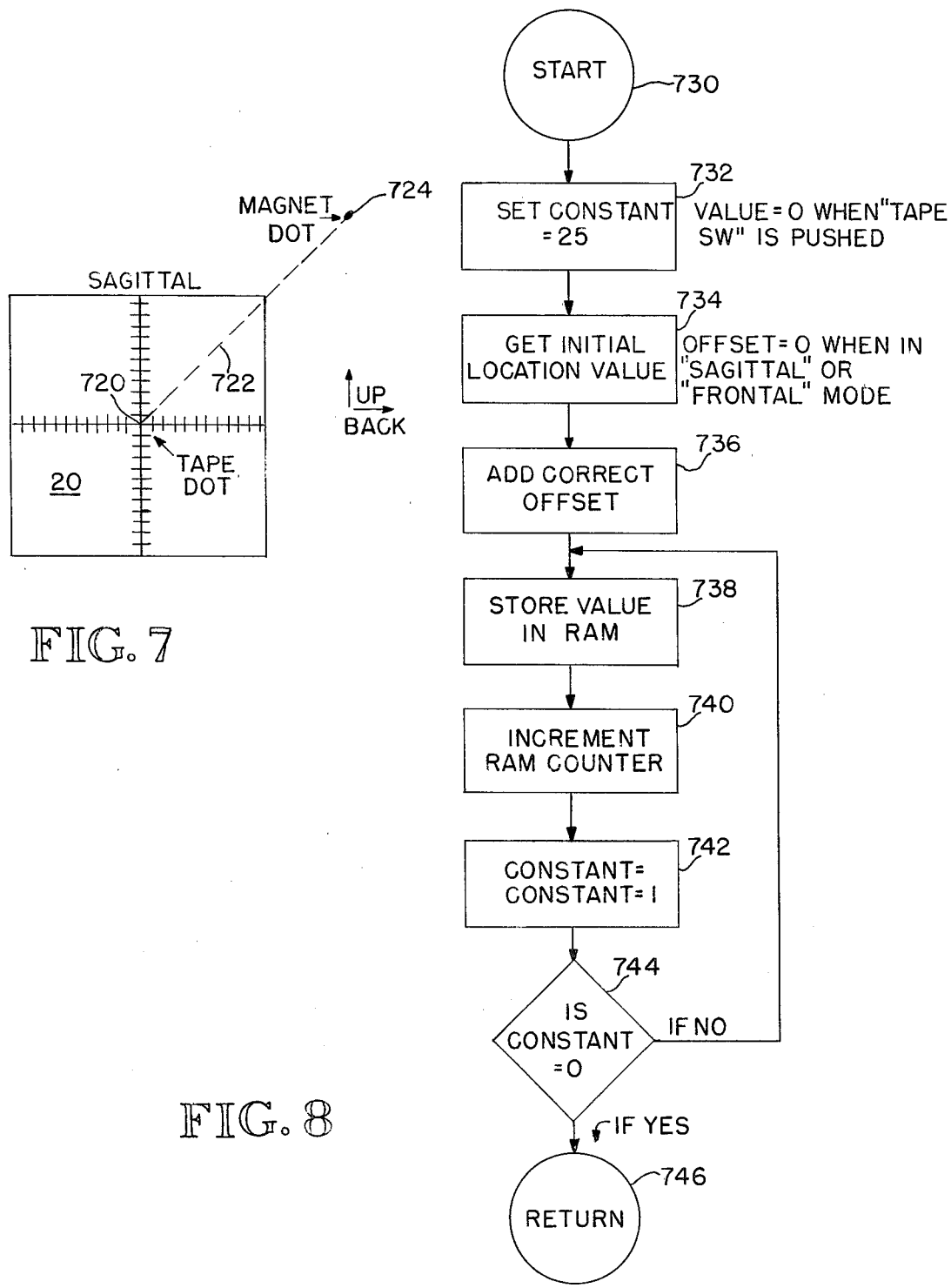
FIG. 7 is a schematic illustrating the manner in which a line is formed on the screen to indicate the direction the frame should be moved for optimum performance.
FIG. 8 is a flow chart of the software controlling the operation of the microprocessor to provide the frame positioning indication illustrated in FIG. 7

As mentioned earlier, the system is capable of generating a sensor positioning indication on the screen 20. The positioning mode is entered by first pressing the tape switch 44 (FIG. 1) and then pressing the erase switch 42. After about two seconds, a dot 720 appears at the center of the screen 20, as illustrated in FIG. 7. The tape switch 44 is then actuated again, followed by pressing the view switch 38, thereby causing a positioning line 722 to appear on the screen 20. The line indicates the direction that the frame 16 should be moved to place it in optimum position. For the example illustrated in FIG. 7, the frame 16 should be moved upwardly and back. When the frame 16 becomes sufficiently close to its optimum position, the line 722 terminates in a dot 724 that indicates the position of the frame relative to its optimum position. As a result, the magnitude as well as the direction required for optimum positioning are displayed to facilitate quick and accurate manipulation of the frame 10.

The positioning indication is provided by a software subroutine that can be entered in either the sagittal or frontal mode. The subroutine, illustrated in flow chart form in FIG. 8, is entered at 730 by pressing the erase switch. A constant indicative of the number of data points stored in the positioning mode is set at 732, which, as illustrated herein, is 25. A zero-volt value is then generated at 734 because the data stored after pressing the tape switch 44 will be equal to zero volts when the erase switch 42 is pressed. This zero-volt data point eventually forms the dot 720 at the center of the screen 20, as explained below. An offset must be added to all data points in the sagittal or frontal mode, as explained above, and this offset is added at 736.

The zero-volt data point is stored in RAM at 738, and the RAM counter is incremented to the next memory location at 740. Finally, the constant that was set at 732 is decremented by one at 742, and, if the new value for the constant is not found to be zero at 744, the program returns to 738 to once again store the zero-volt data point in RAM. The subroutine loops in this manner until a number of the zero-volt data points corresponding to the constant set at 732 (e.g., 25) are stored in RAM. The subroutine then returns to the main program via 746.

The tape switch is then pressed, followed by the view switch 38, thereby causing the system to alternately display the stored zero-volt data points and the real-time data point indicative of the position of the magnet. The line 722 is generated on the screen 20 because, by pressing the view switch 38, the trace on the screen is not blanked while transitioning between the center dot 720 and the dot 724 indicative of the real-time position of the magnet.

I claim:

1. A system for storing and displaying a kinesiograph waveform on which a subsequently occurring, corresponding kinesiograph waveform may be superimposed, comprising:

sample means for periodically sampling at least one kinesiograph waveform;

analog-to-digital converter means for generating as digitized samples respective digital words indicative of the magnitude of said samples;

a random access memory;

addressing means for selectively writing a set of said digitized samples for each waveform in predetermined locations of said random access memory and then repetitively reading at least one of said sets of digitized samples from said random access memory in a predetermined order;

first digital-to-analog converter means receiving the digitized samples read out from said memory and generating a voltage having a magnitude proportional to the digital value of said samples;

display means including first and second outputs having a screen on which a spot is displayed at a location in two orthogonal directions corresponding to the magnitude of signals applied to said first and second inputs;

first switch means for selecting the kinesiograph waveform to which each set of samples read from said memory corresponds, said switch means further scaling and offsetting said kinesiograph waveform to match the scale and offset of the corresponding set of samples read from said memory;

first multiplexer means alternately applying the output of said digital-to-analog converter means and each kinesiograph waveform selected by said switch means to the first input of said display means such that each kinesiograph waveform is superimposed in real time on the screen of said display with a recorded kinesiograph waveform; and means for applying a signal to the second input of said display means having a predetermined relationship to the manner in which said multiplexer means applies signals to the first input of said display means.

2. The system of claim 1 wherein said addressing means writes samples of a plurality of kinesiograph waveforms and respective blocks of said memory in chronological order and reads samples from memory locations in at least one of said blocks as selected by an address word, said switch means being controlled by the most significant bits of said address word such that said address word reads out samples from the block of memory corresponding to the kinesiograph waveform which the switch means applies to multiplexer means, thereby superimposing a real-time kinesiograph waveform on the same kinesiograph waveform occurring earlier in time.

3. The system of said claim 2 wherein said means for applying a signal to the second input of said display means comprise:
second digital-to-analog converter means receiving digitized samples from memory locations in at least one of said blocks and generating a voltage having a magnitude proportional to the digital value of said samples;
second switch means for selecting the kinesiograph waveform to which each set of samples read from said memory corresponds, said switch means further scaling and offsetting said kinesiograph waveform to match the scale and offset of the corresponding set of samples read from said memory, said switch means being controlled by the most significant bits of said address word so that said address word reads out samples from the block of memory corresponding to the kinesiograph waveform which the switch means applied to said second multiplexer means; and
second multiplexer means alternately applying the output of said second digital-to-analog converter means and the kinesiograph waveform selected by said second switch means to the second input of said display means so that a pair of kinesiograph waveforms are displayed with respect to each other in real time in superposition with a stored pair of the same kinesiograph waveforms.

4. The system of claim 1 wherein said means for applying a signal to the second input of said display means comprise:
an oscillator;
counter means having a clock input receiving the output of said oscillator to increment said counter;
second digital-to-analog converter means applying a voltage to the second input of said display means having a magnitude proportional to the value of a digital word applied to its input; and
second multiplexer means applying the output of said counter to said second digital-to-analog converter in a sweep mode and applying digitized samples from memory locations in at least one of said blocks in an X-Y mode whereby a real-time kinesiograph waveform may be superimposed on a stored kinesiograph waveform displayed with respect to either time or another kinesiograph waveform.

5. The system of claim 4 wherein said addressing means writes samples of a plurality of kinesiograph waveforms in respective blocks of said memory in chronological order and reads samples from memory locations in at least one of said blocks as selected by an address word, said system further including second switch means for selecting the kinesiograph waveform to which each set of samples applied to said multiplexer means corresponds, said first and second switch means being controlled by the most significant bits of said address word such that said address word applies samples to the first digital-to-analog converter and the second multiplexer means from the block of memory corresponding to the kinesiograph waveforms which respective first and second switch means select, said system further including third multiplexer means alternately applying the output of said second digital-to-analog converter means and the kinesiograph waveform selected by said second switch means to the second input of said display means so that real-time kinesiograph waveforms are superimposed on the same kinesiograph waveforms occurring earlier in time and displayed with respect to either time or another kinesiograph waveform.

6. The system of claim 1 wherein said means for applying a signal to the second input of said display means comprise:
an oscillator;
counter means having a clock input receiving the output of said oscillator to increment said counter throughout a predetermined range, the output of said counter means selecting the memory location from which digitized samples are read from said random access memory and applied to said first digital-to-analog converter means;
second digital-to-analog converter means receiving the output of said counter means and applying a voltage to the second input of said display means having a magnitude corresponding to the output of said counter means;
means for periodically presetting said counter to one of a plurality of values X given by the formula: $X=(X_n-X_0)/N$, where $X_0$ is the output of said counter means indicative of the lowest memory location, $X_n$ is the output of said counter means indicative of the highest memory location, and N is an integer greater than 1; and
means for scaling and offsetting the output of said second digital-to-analog converter means so that the output of said digital-to-analog converter means causes the spot of said screen to move between opposite edges of said screen, thereby displaying an expanded portion of said kinesiograph waveform with respect to time.

7. The system of claim 1, further including a microprocessor system for controlling the operation of said system, including a non-volatile, read-only memory having predetermined data stored therein, a volatile random access memory, a processing unit and means for resetting said processing unit, either manually or as power is initially applied thereto, said microprocessor system further including means for determining whether said reset is caused manually or by a power-up, comprising means for reading said predetermined data from said read-only memory and writing said data into a predetermined location in said random access memory upon power-up of said processing unit and means for checking said predetermined location in said random access memory for the presence of said predetermined data responsive to said processing unit being reset whereby the presence of said data in said random access memory indicates a manual reset and the lack of said data in said random access memory indicates a power-up-induced reset.

8. The system of claim 1 wherein said memory may be erased by writing predetermined bits in all memory locations, said system further including blanking means for blanking the spot on the screen of said display means when the digitized samples read from said memory are equal to said predetermined bits, thereby preventing said display means from writing on said screen when said memory has been erased.

9. A system for diagnosing irregularities and defects in mandibular movements, comprising:
kinesiograph means for generating first and second kinesiograph waveforms indicative of respective mandibular movements in two orthogonal directions;

storage means for recording said kinesiograph waveforms and repetitively generating respective output signals corresponding thereto; and display means having a screen on which first and second kinesiograph signals are displayed with respect to each other simultaneously and in superposition with the corresponding output signals of said storage means such that pairs of real-time kinesiograph waveforms are individually displayed as they occur in superposition with single, earlier occurring, identical pairs of kinesiograph waveforms.

10. The system of claim 9 wherein said storage means includes a random access memory divided into a plurality of memory blocks in which samples of a plurality of respective kinesiograph waveforms are stored in locations identified by respective addresses and wherein said display means includes switch means receiving all of said kinesiograph waveforms and selecting one of said kinesiograph waveforms as an output, and mutliplexer means alternately displaying the output of said switch means and an analog signal indicative of the sample of a kinesiograph signal selected by said address, said switch means being controlled by the most significant bits of said address whereby said address selects corresponding portions of the same real-time and stored kinesiograph waveforms for display on said screen.

11. The system of claim 9, further including positioning means for aligning an array of kinesiograph sensors with a magnet secured to the mandible of a patient, comprising:

means for displaying a point on said screen indicative of said sensor array; and means for displaying a line on said screen extending from said point in a direction indicative of the position of said sensor array with respect to said optimum position.

12. The system of claim 11, further including means for displaying a dot on said screen at the end of said line opposite the dot that is indicative of the optimum position of said sensor array, thereby providing an indication of the magnitude as well as the direction that said sensor array is spaced from said optimum position.

13. The system of claim 11 wherein said sensors are bilateral in nature so that they generate an output signal differentially and wherein said optimum position point on said screen is a zero-volt data point.

14. The system of claim 13 wherein said line is displayed by applying a signal to said screen indicative of the actual location of said sensor array and unblanking the trace on said screen as it transitions between said zero-volt data point and a point indicative of the actual location of said sensor array.

15. In a microprocessor system including a non-volatile, read-only memory having predetermined data stored therein, a volatile random access memory, a processing unit and means for resetting said processing unit, either maually or as power is initially applied thereto, means for determining whether said reset is caused manually or by a power-up, comprising means for reading said predetermined data from said read-only memory and writing said data into a predetermined location in said random access memory upon power-up of said processing unit, and means for checking said predetermined location in said random access memory for the presence of said predetermined data responsive to said processing unit being reset whereby the presence of said data in said random access memory indicates a manual reset and the lack of said data in said random access memory indicates a power-up-induced reset.

* * * * *